United States Patent [19]
Garth et al.

[11] Patent Number: 5,211,185
[45] Date of Patent: May 18, 1993

[54] HEAD IMMOBILIZER

[75] Inventors: Geoffrey Garth; James Traut, both of Long Beach, Calif.

[73] Assignee: California Medical, Long Beach, Calif.

[21] Appl. No.: 696,032

[22] Filed: May 6, 1991

Related U.S. Application Data

[63] Continuation-in-part of Ser. No. 659,076, Feb. 22, 1991, which is a continuation-in-part of Ser. No. 571,010, Aug. 6, 1990, which is a continuation of Ser. No. 275,255, Nov. 23, 1988, which is a continuation-in-part of Ser. No. 243,356, Sep. 12, 1988.

[51] Int. Cl.⁵ ............................................. A61B 19/00
[52] U.S. Cl. ..................................... 128/870; 128/876; 602/17; 602/18; 5/628
[58] Field of Search ............... 128/857, 869, 870, 163, 128/87 B, 89 R, 89 A, 76 R, 78, 876; 5/82 R, 434–437

[56] References Cited

U.S. PATENT DOCUMENTS

| | | | |
|---|---|---|---|
| 3,397,688 | 8/1968 | Gottfried | 128/869 X |
| 3,469,268 | 9/1969 | Phillips | 128/870 X |
| 3,889,668 | 6/1975 | Ochs et al. | 128/870 |
| 3,933,154 | 1/1976 | Cabansag | 128/870 |
| 3,957,262 | 5/1976 | McReynolds | 5/437 X |
| 4,182,322 | 1/1980 | Miller | 128/869 |
| 4,299,211 | 11/1981 | Doynow | 128/89 R |
| 4,422,454 | 12/1983 | English | 128/870 |
| 4,589,407 | 5/1986 | Koledin et al | 128/869 |
| 4,594,999 | 6/1986 | Nesbitt | 128/869 X |
| 4,665,908 | 5/1987 | Calkin | 128/870 |
| 4,928,711 | 5/1990 | Williams | 128/869 |
| 4,964,418 | 10/1990 | Wilson | 128/857 |

FOREIGN PATENT DOCUMENTS 01513  6/1981  World Int. Prop. O. ........... 128/869

Primary Examiner—Robert A. Hafer
Assistant Examiner—Gregory M. Stone
Attorney, Agent, or Firm—Kenyon & Kenyon

[57] ABSTRACT

A head immobilization device is disclosed comprising a foundation portion and a restraining portion. The foundation portion comprises a foundational panel and an adhesive first spine board engaging element situated on the lower surface of the foundation panel. The restraining portion comprises a base panel, two side panels extending laterally from the outer sides of the base panel, and at least one band of material for affixing the side panels to each other in suitable conformance with the patient's head.

8 Claims, 12 Drawing Sheets

HEAD IMMOBILIZER

This application is a continuation-in-part of co-pending application Ser. No. 07/659,076, filed Feb. 22, 1991, which is a continuation-in-part of co-pending application Ser. No. 07/571,010, filed Aug. 6, 1990, which was a continuation of application Ser. No. 07/275,255, filed Nov. 23, 1988, which is a continuation-in-part of application Ser. No. 07/243,356, filed Sep. 12, 1988.

BACKGROUND OF THE INVENTION

This invention relates to a new and improved device for immobilizing a patient's head during emergency treatment or transport.

Emergency medical personnel are frequently called upon to treat patients who may have suffered injury to the cervical spine or may be at risk for cervical spine injury if not properly handled during treatment and transport. Conventionally, such patients are placed in a cervical extrication collar (e.g., those shown in U.S. Pat. No. 32,219) which restricts the patient's head from moving out of the vertical erect position. Often, however, such collars do not sufficiently restrict movement of the cervical spine. It is therefore desirable to use additional measures to restrict such movement.

Presently, emergency medical personnel use a variety of "jury-rigged" means to immobilize the patient's head, including placing sand bags or large foam blocks at the sides of the head. Previous devices include those shown in U.S. Pat. Nos. 3,897,777, 4,589,407, 4,594,999 and 4,718,412. Unfortunately, all of these devices are either cumbersome, ineffective or uneconomical for use in large numbers. Furthermore, previous devices also nearly cover the sides of the patient's head, thus prohibiting full assessment of the patient's condition which may deteriorate during transport.

U.S. Pat. No. 4,964,418 to Wilson discloses a device for immobilizing a patient's head when placed on a spine board. Such devices have been sold commercially under the tradename "HeadVise". Similar but distinct devices have also been sold by California Medical Products, Inc., Long Beach, Calif. under the tradename "HeadBed".

Jerome Emergency Medical Products, Mt. Laurel, N.J., has also sold a head immobilization device under the name "HedLoc". However, such product has certain disadvantages in use. First, the device contains a chin flap which impedes easy access to portions of the side of the patient's head and neck, such that once a patient has been placed in the device certain injuries in those areas may be unobservable or inaccessible for treatment without disrupting the desired immobilization of the patient's head. The HedLoc device also uses two hook and loop straps to secure the device to a spine board. To attach the device to the board these straps must be slid under the board and then tightened around the surface of the board. As a result, the device can only be placed on the board prior to positioning of a patient on the board; once a patient is placed on the board it is undesirable to move or lift the board in order to secure the device to the board under the patient's head. Additionally, the storage of a spine board with a previously attached device of this type is often not possible in an ambulance or other emergency vehicle due to extreme storage space limitations as a result of the increase in board thickness caused by the device.

The present invention overcomes certain drawbacks of the previous devices and provides effective, efficient and economical means for immobilizing a patient's head during treatment and transport.

SUMMARY OF THE INVENTION

In accordance with the present invention, a head immobilization device is disclosed comprising a foundation portion and a restraining portion. The foundation portion comprises a foundation panel and may in certain embodiments also comprise a spine board engaging means situated on the bottom surface of the foundation panel. The restraining portion comprises a base panel contiguous with the central portion of the foundation panel, and two side panel portions extending laterally from the outer sides of the base panel. Each side panel has a free end opposite the end of the panels which connects to the base panel. At least one of the side panels has a first engaging means associated with its free end for engagement of the opposite side panel and for securing the side panels into secure and proper conformation so as to at least partially immobilize the head of a patient placed between the side panels.

In certain preferred embodiments, the side panel portions are each further subdivided into a plurality of subpanels separated by score lines that allow each panel to hinge with respect to its adjacent panel. This arrangement allows the side panels to comport to the shape of the patient's head. The side panel portions have near their outer portions engaging means for enabling one to securely place the subpanels of the side panels in proper conformation to restrain the head of a patient. Preferably, the engaging means employed comprises a strip of single-sided adhesive tape. While a single strip is preferred, a second strip located on the other side panel may be provided as well. In other preferred embodiments, a belt or strap having other forms of fastener structure, such as hook-and-loop fastener structure for mating with a corresponding hook-and-loop type element affixed to the opposite side panel, could be used.

Although separate sheets of material may be used to form the foundation and restraining portions of the device, in preferred embodiments the foundation portion and the restraining portion are constructed from the same sheet of material such that the base panel, foundation portion, and restraining portion all lie in a common plane. Such a construction enables greater economies in production than would be realized in devices using a greater number of individual parts.

DESCRIPTION OF THE PREFERRED EMBODIMENTS

Figure 1:
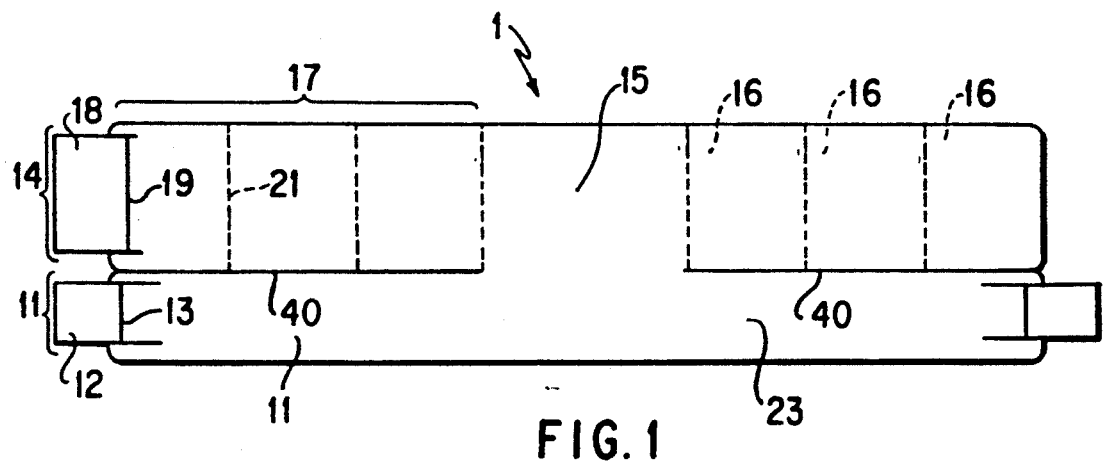
FIG. 1 is a top plan view of one embodiment of the present invention in its unassembled configuration.
Figure 2A:
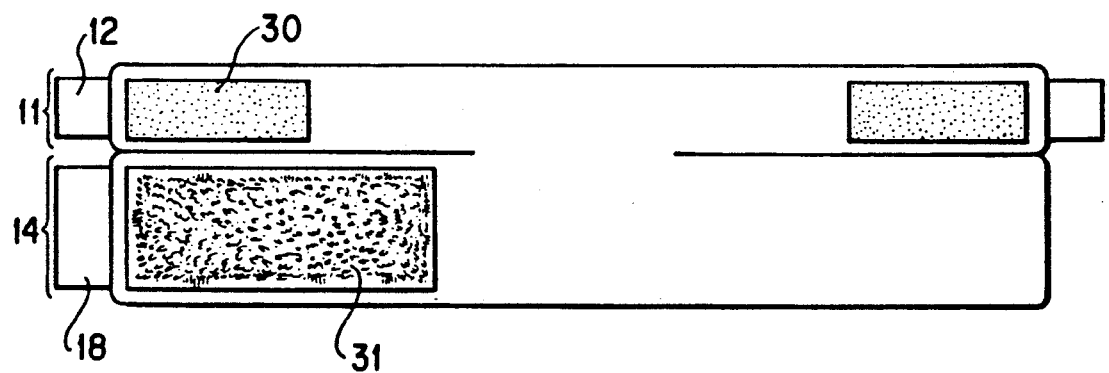
FIG. 2a is a bottom plan view of the embodiment of FIG. 1 having a single restraining means 31.
Figure 2B:
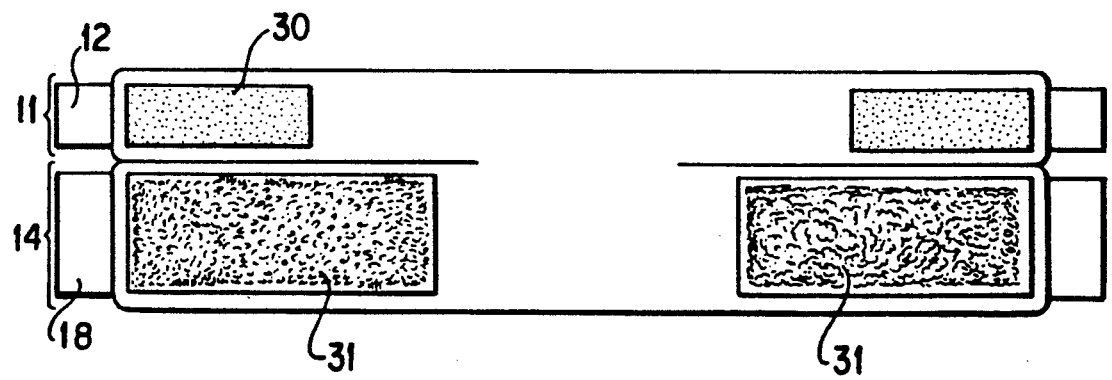
FIG. 2b is a bottom plan view of an embodiment of the device equipped with dual restraining means 31.

FIGS. 1 and 2 depict the basic form of the present invention. The device 1 has a generally rectangular configuration in which a pair of inwardly extending cuts 40 running parallel to the long edge of the rectangle divide the device into an upper restraining portion 14 and a lower foundation portion 11. These cuts 40 extend only partially in from the outer edges, terminating at a centrally disposed base panel 15. The base panel 15 is located at the center of the restraining portion 14. A side panel portion 17 extends laterally from each side of the base panel 15, and is made up of a plurality of subpanels 16. Score lines 21 separate adjacent subpanels. The score lines 21 make the side panels 17 more flexible such that they may be more closely conformed to the shape of the patient's head to achieve a close fit.

In the preferred embodiment shown in FIGS. 1 and 2a, the various features of the device lie within the plane of a single sheet of material. The foundation portion 11 and restraining portion 14 are formed from the same sheet of material and, therefore, do not need to be joined by other means. In alternative embodiments the foundation and restraining portions of the device can be non-coplanar and/or made from separate sheets of suitable material.

The foundation panel 23 has near the extremities of its lower surface adhesive elements 30 to facilitate the anchoring of the device to the spine board. The adhesive element can take any conventional form. A preferred form is to use double-sided adhesive tape. The side not facing the foundation panel is backed with a removable sheet of backing material that terminates in a quick-pull tab portion 12. This quick-pull structure may take any conventional form, such as a doubled over sheet of backing material that begins near the outer edge of the adhesive element 30, continues inwardly to the inner edge of the adhesive element, and then doubles back past the outer portion of adhesive element 30, where it extends through a slot 13 cut into the foundation panel. From there, it continues to its termination in a tab portion protruding into the upper side of the foundation panel.

The bottom portion of one of the side panels 17 is equipped with a band of restraining material 31. This material may take the form of tape, Velcro, or other conventional fastener structure. (Where Velcro is used, the appropriate mated hook or loop structure must, of course, be placed on the bottom side of the opposite side panel.) Where tape is used, the tape may be equipped with backing material on its sticky side. To facilitate storage of a sufficient length of tape in an uncluttered manner, the tape may be kept in folded configuration beneath one of the side panels. A backing material may be employed in the manner discussed with respect to the adhesive tape on the bottom of the foundation panel. One end of this backing material may be inserted through a slot 19 near the outer portion of a side panel so that its free end protrudes into the upper region of the device.

The tape is of sufficient length so that when the side panels are brought into conformance with the patient's head, the tape can be pulled through slot 19 by tab 18 in an action that separates the backing from the tape. The tape is then wrapped over the forehead of the patient and brought into operative engagement with the other side panel of the device. (See FIGS. 3b and 4a.) Alternatively, this can be accomplished in a separate procedure.

Figure 3A:
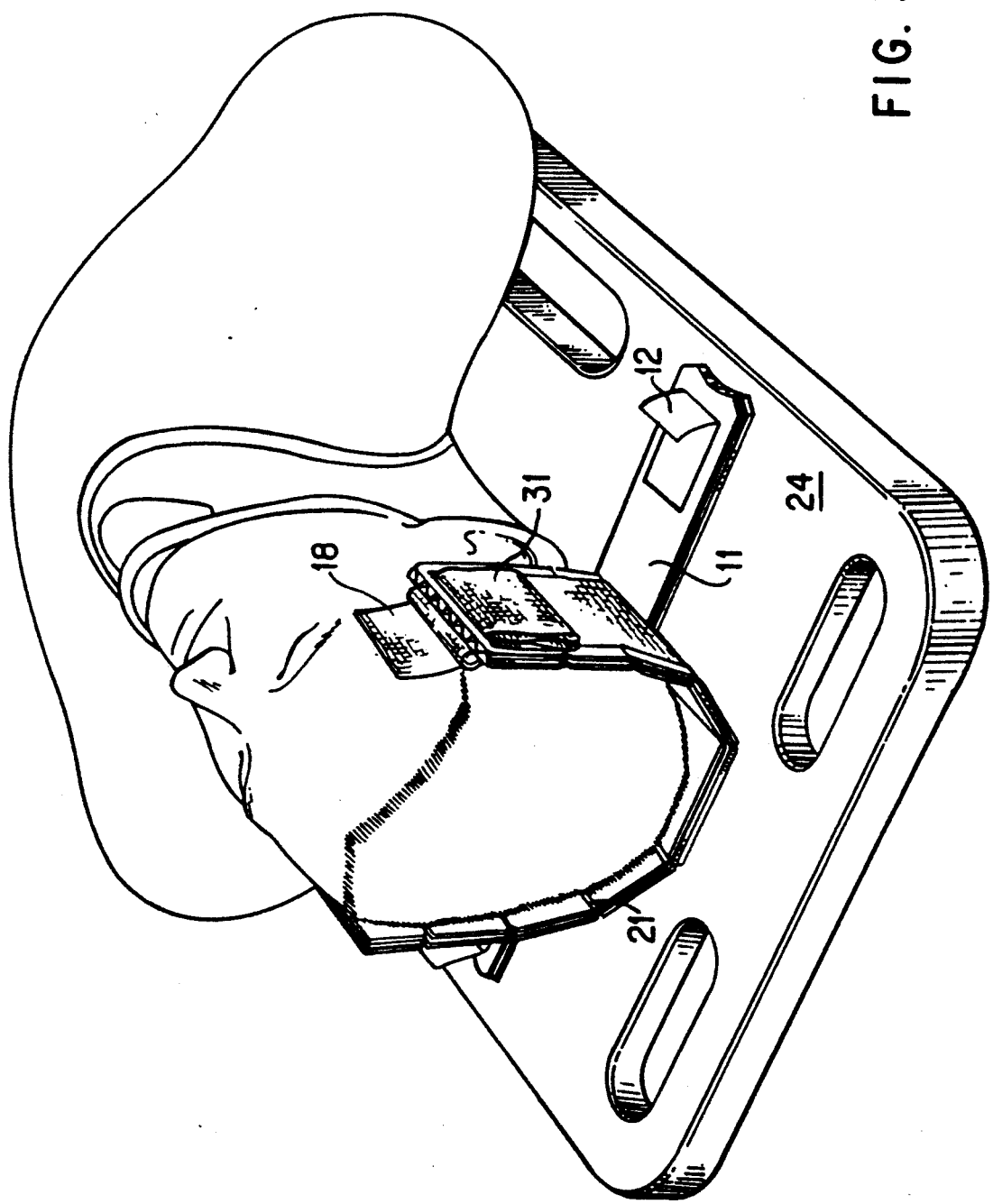
FIGS. 3a, 3b, 4a, and 5 are perspective views of the embodiment of FIG. 1 as it is used and placed about the patient's head.
Figure 3B:
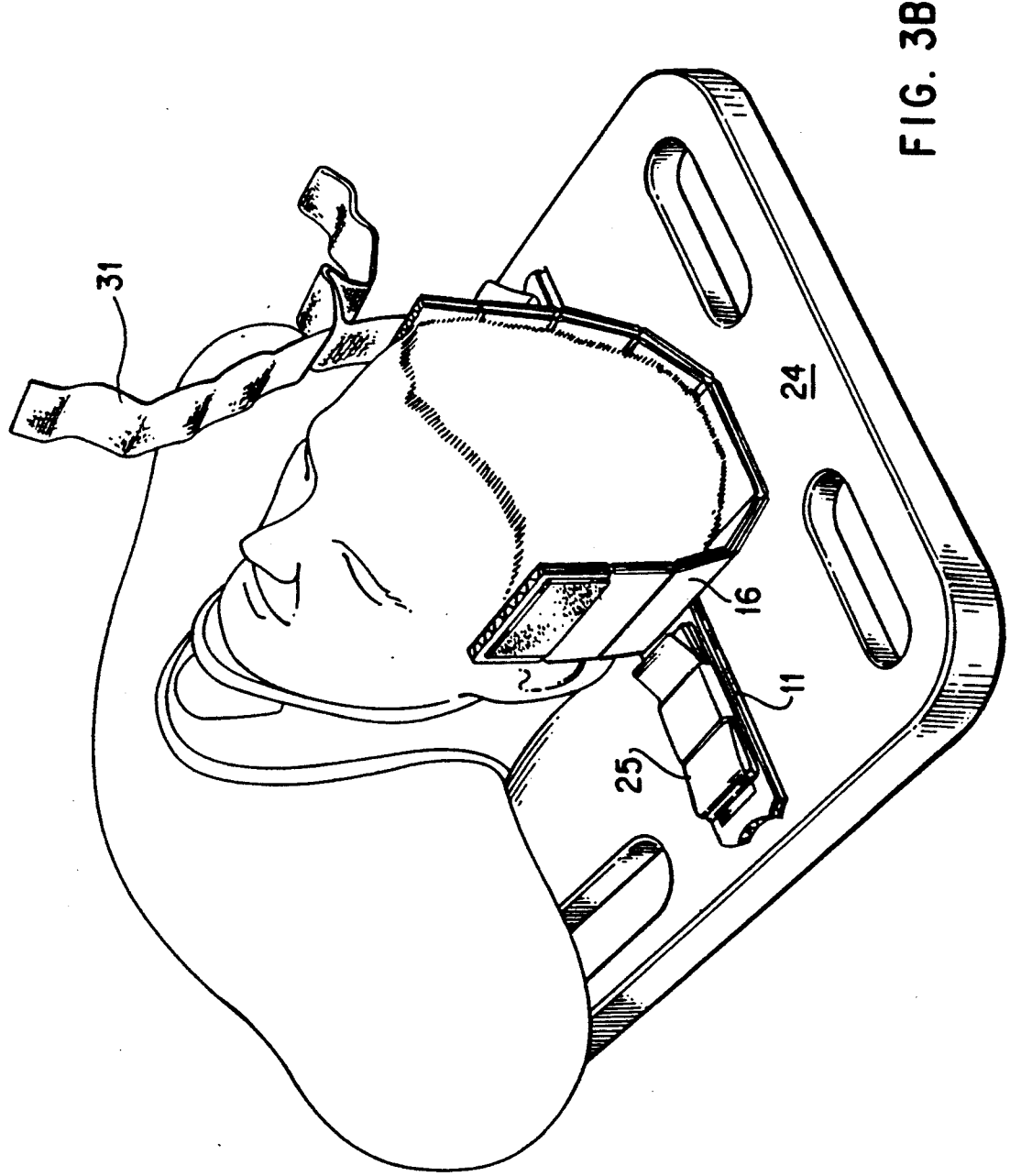
Figure 4A:
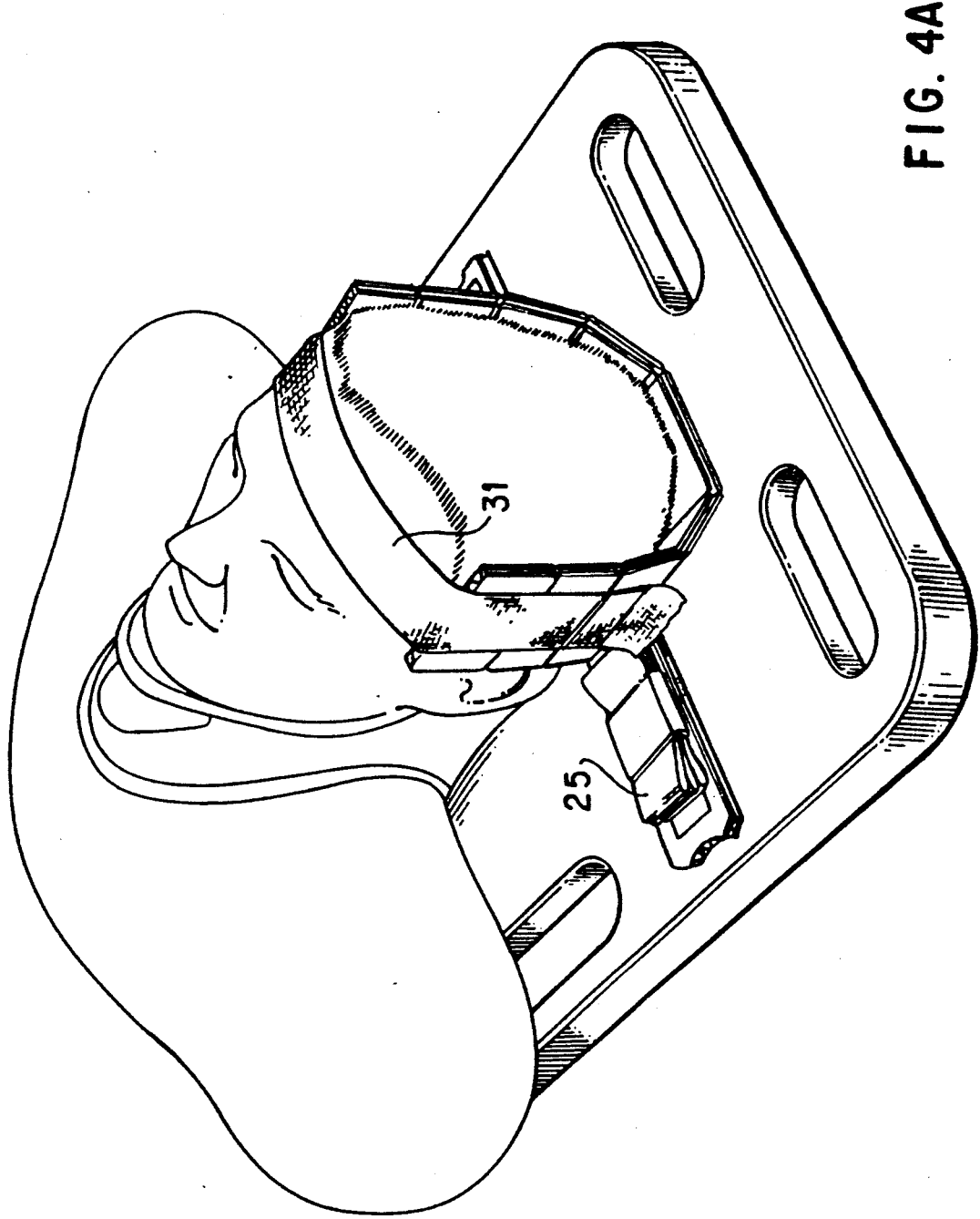
Figure 4B:
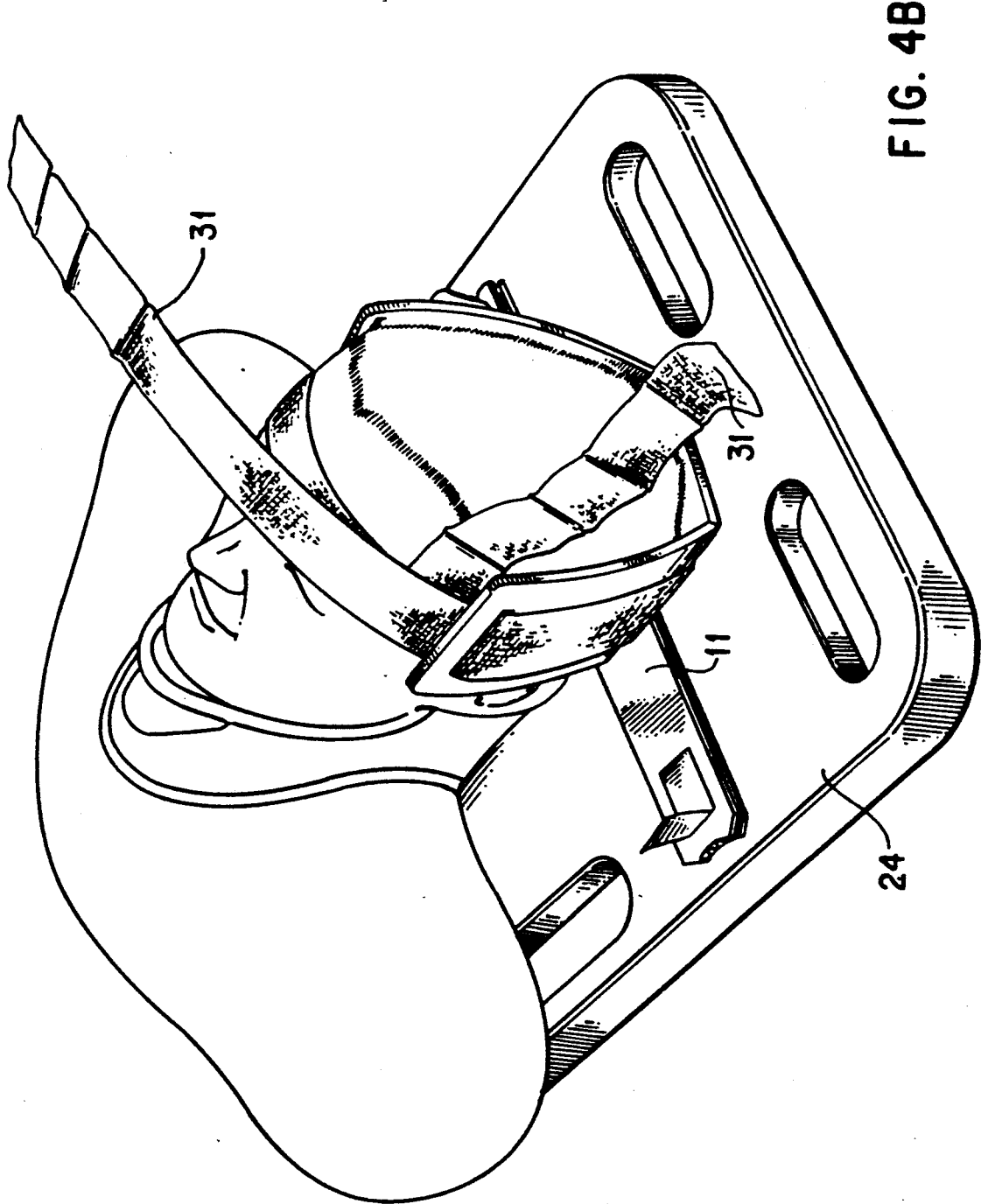
FIG. 4b shows the device of FIG. 1 as used with an extra band of restraining material.

FIGS. 3a through 8 show a device of the present invention in use. The device is slid under the patient's head such that the head rests on the base panel 15. Once the device is properly positioned with respect to the patient's head and the spine board 24, the two lateral side panels 17 of the restraining portion 14 of the device are brought into the proper conformation (e.g., as shown in FIGS. 3a, 3b, and 4a) such that the side panels 17 fit snugly against the patient's head. As shown in these figures, the length of tape stored along the underside of the side panel is brought forward by pulling on tab 18, which pulls the tape through slot 19 and also exposes the adhesive side of the tape. This adhesive side is then wrapped across the patient's forehead in the manner deemed most appropriate for the patient's condition, and is brought into engagement with the other side panel. When this is accomplished, the patient's head is prevented from rotating. (One may optionally employ such fixation structure on both side panels so that the head is constrained by two lengths of tape, each terminating on the other side panel, as shown in FIG. 4b.) Then, the adhesive 30 beneath each side of the foundation panel can be engaged such that the device is anchored to the spine board 24. Thus the device of the present invention can be anchored to the spine board after it is properly attached to the patient's head. This ability of the devices of the present invention is in contrast with prior devices which had to be attached to the spine board prior to positioning of the patient on the board and which could not be moved with respect to the patient's head once the patient was on the board.

Figure 5:
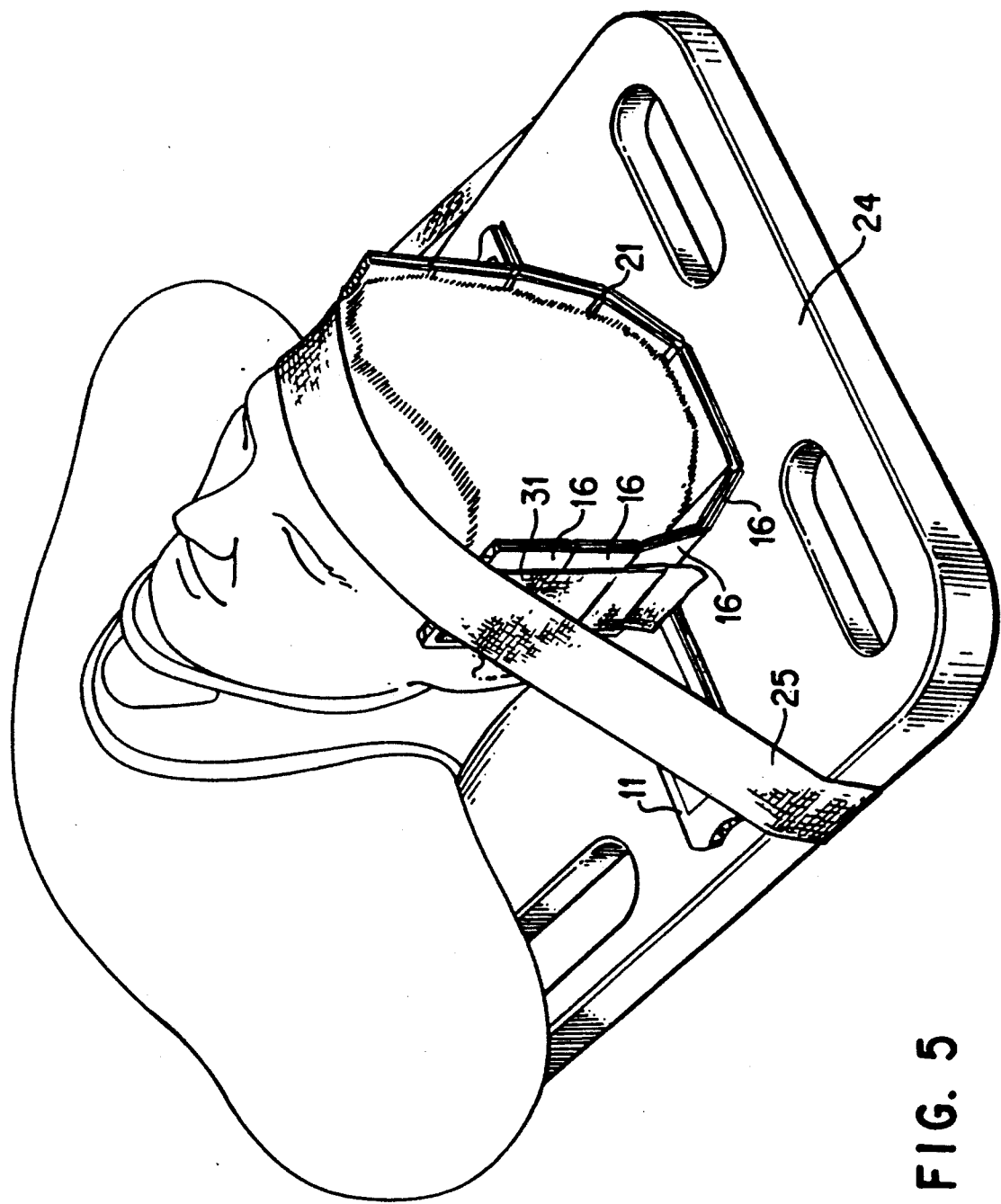

As shown in FIG. 5, an additional piece of adhesive tape 25 (or a strap or other means) is preferably (but optionally) used to further constrain the patient's head. Tape 25 is extended from one side of the spine board across the patient's head to the other side of the spine board, thereby eliminating any remaining rotation, flexion or lateral motion, and greatly limiting the straining forces on the device itself. In certain embodiments, additional tape 25 can be provided or packaged as part of the entire device. (This optional feature is shown in a stored configuration in FIGS. 3b and 4a.)

The devices of the present invention provide the advantage of achieving immobilization of the patient's head without significantly impeding treatment of the patient's injuries. The side panels of the device cover only a portion of the patient's cranium. Thus, the majority of the sides of the patient's head and neck are exposed for easy observation and treatment of injuries in those areas.

Figure 6:
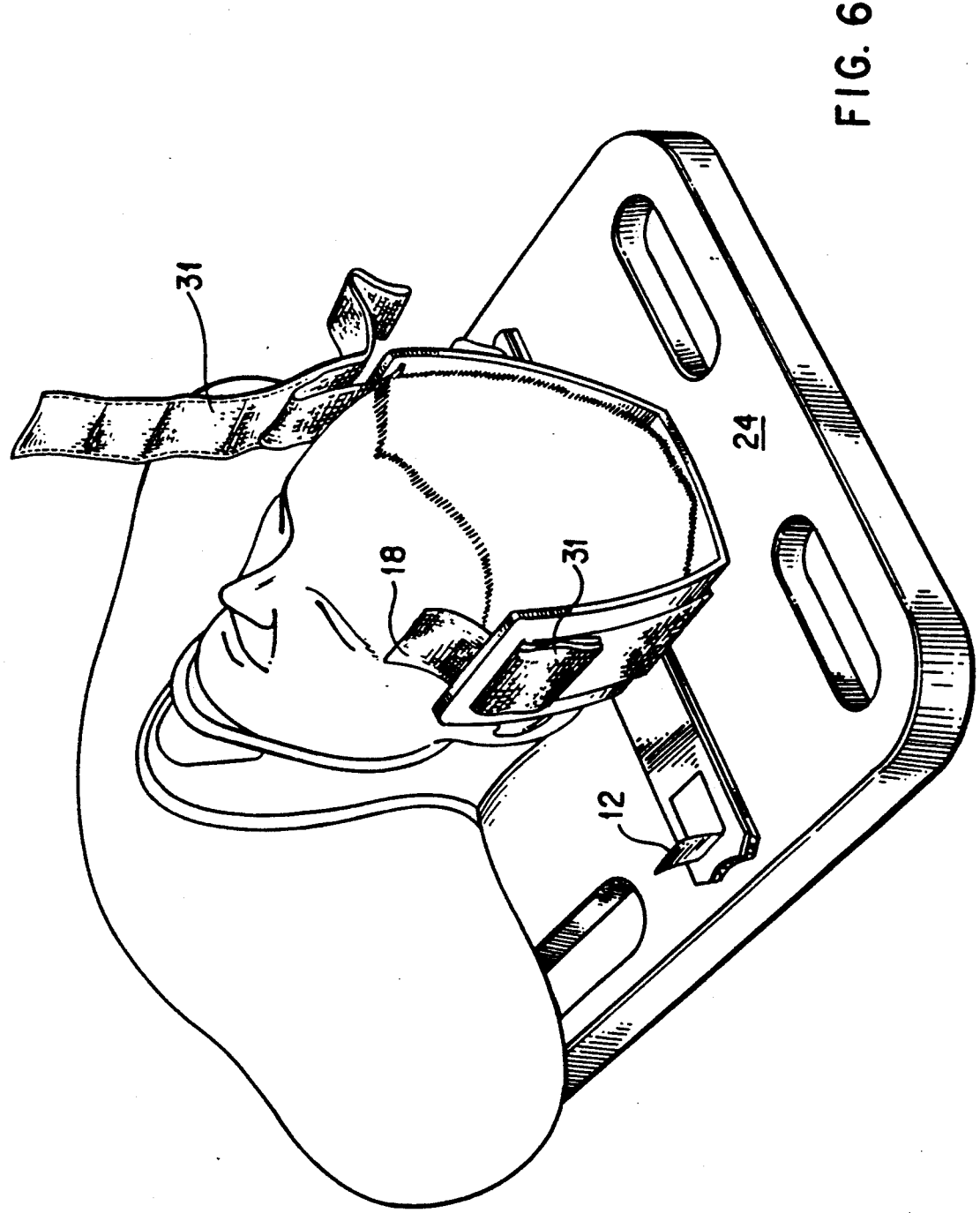
FIGS. 6 through 8 are perspective views of another embodiment using longer restraining means and how it is used about a patient's head.
Figure 7:
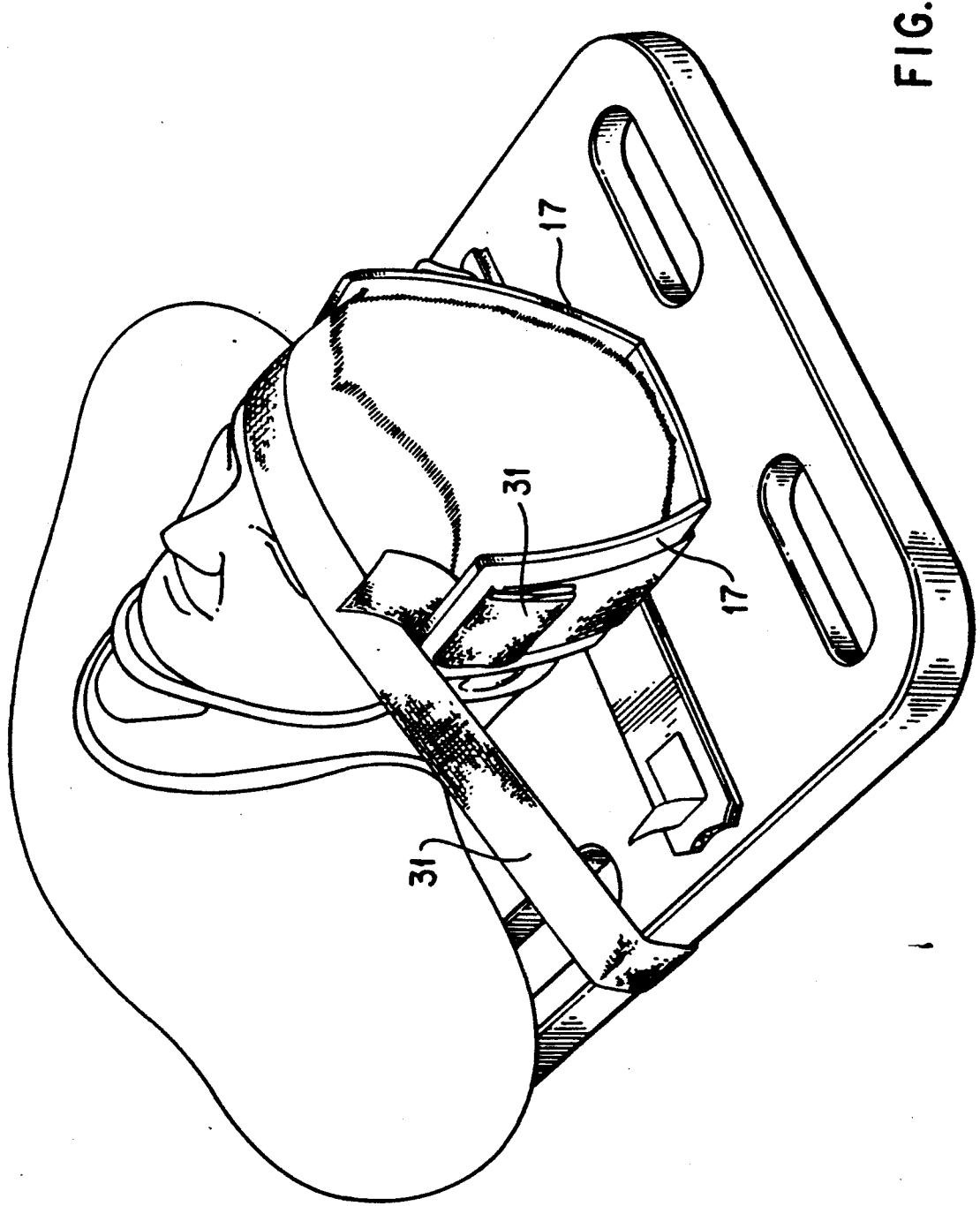
Figure 8:
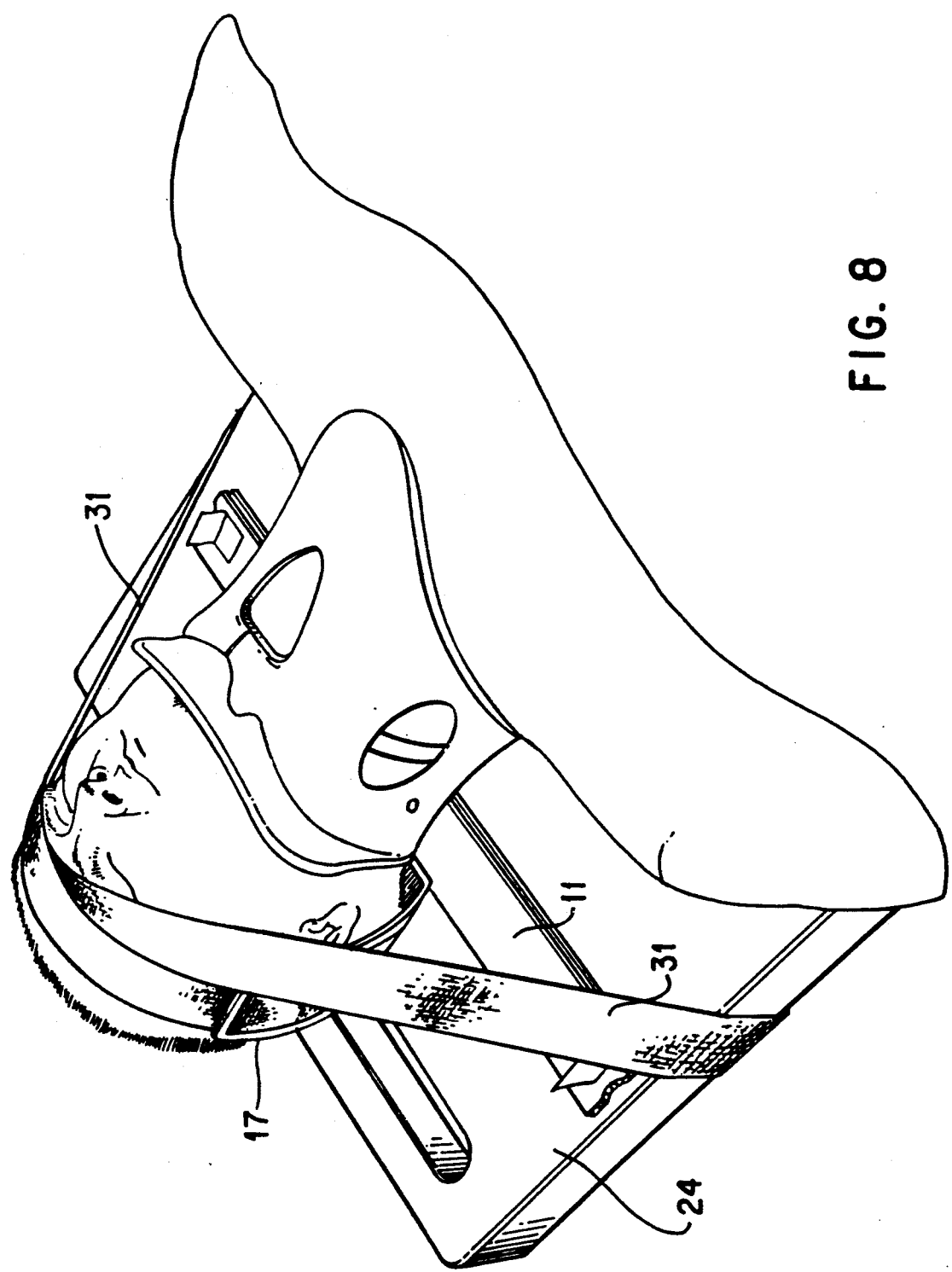

FIGS. 6–8 illustrate an alterative embodiment in which each side panel is equipped with a length of tape of sufficient length that it can be wrapped across the patient's forehead and extended onward to the underside of the opposite side of the spine board.

Using either of the taping configuration shown in FIGS. 5 or 8 in connection with a device of the present invention provides a restraint which allows virtually no movement of the patient's head. The patient's head is immobilized as follows. First, with the application of the first strap or piece of tape, circumferential contact is made with the patient's head such that the head cannot move significantly with respect to tape 31 and base panel 15 such that a point on the back of the patient's head is immobilized with respect to the imaginary line formed by the patient's spine. With the application of the second strap or piece of tape from one edge of the spine board, across the forehead (over the first piece of tape) and over to the opposite side of the spine board, a point on the front of the patient's head is immobilized with respect to the imaginary line formed by the patient's spine. The combination of these two straps or pieces of tape provides essentially complete restriction in flexion, rotation and lateral motion. This restraint configuration can also be achieved using the arrangement of tapes or straps shown in FIGS. 6 or 7. Other means for achieving such immobilization, including without limitation various arrangements of straps, can also be used in connection with devices of the present invention to achieve the desired degree of immobilization.

Figure 9:
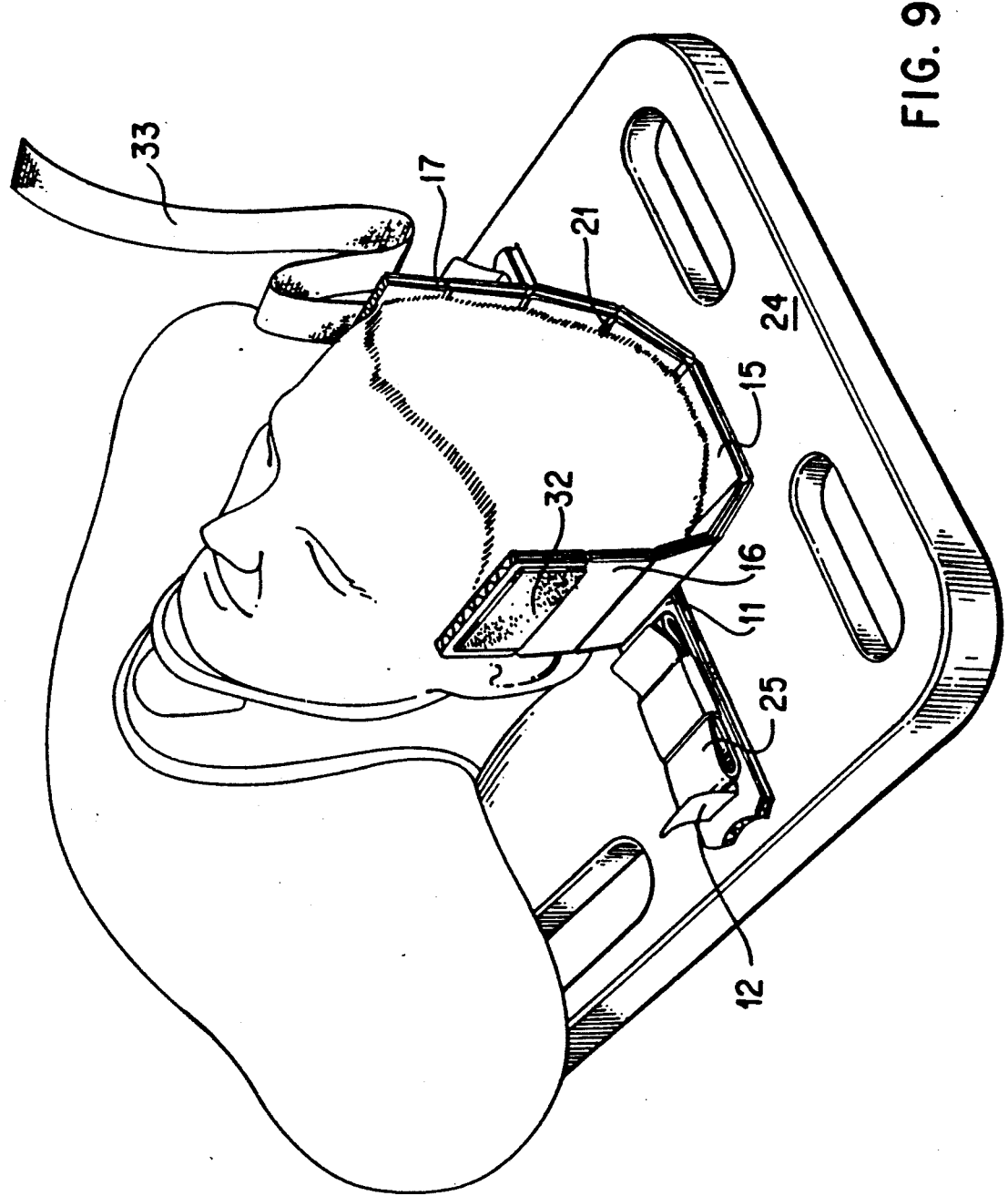
FIGS. 9 through 11 are perspective views of a further embodiment employing other restraining means.
Figure 10:
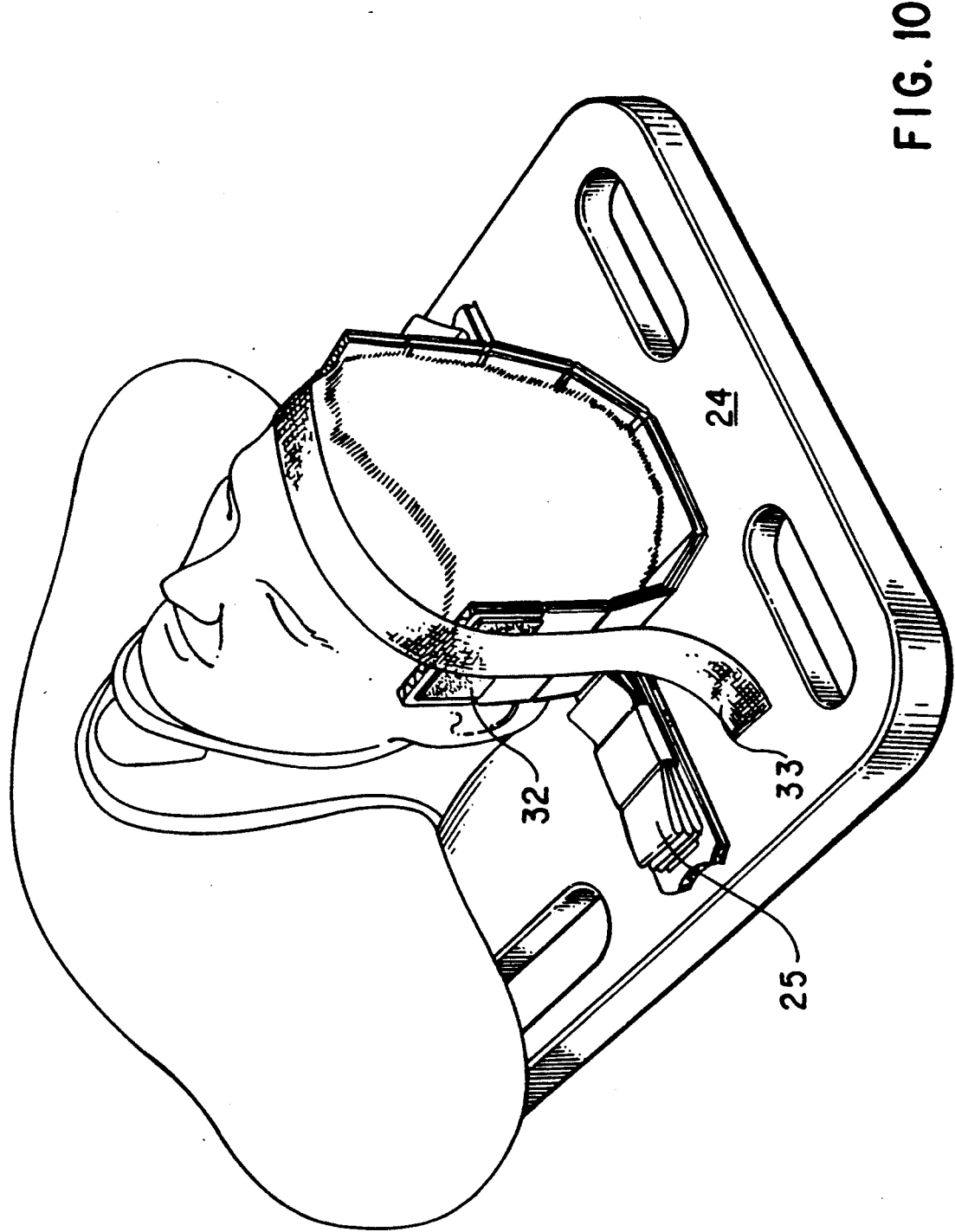
Figure 11:
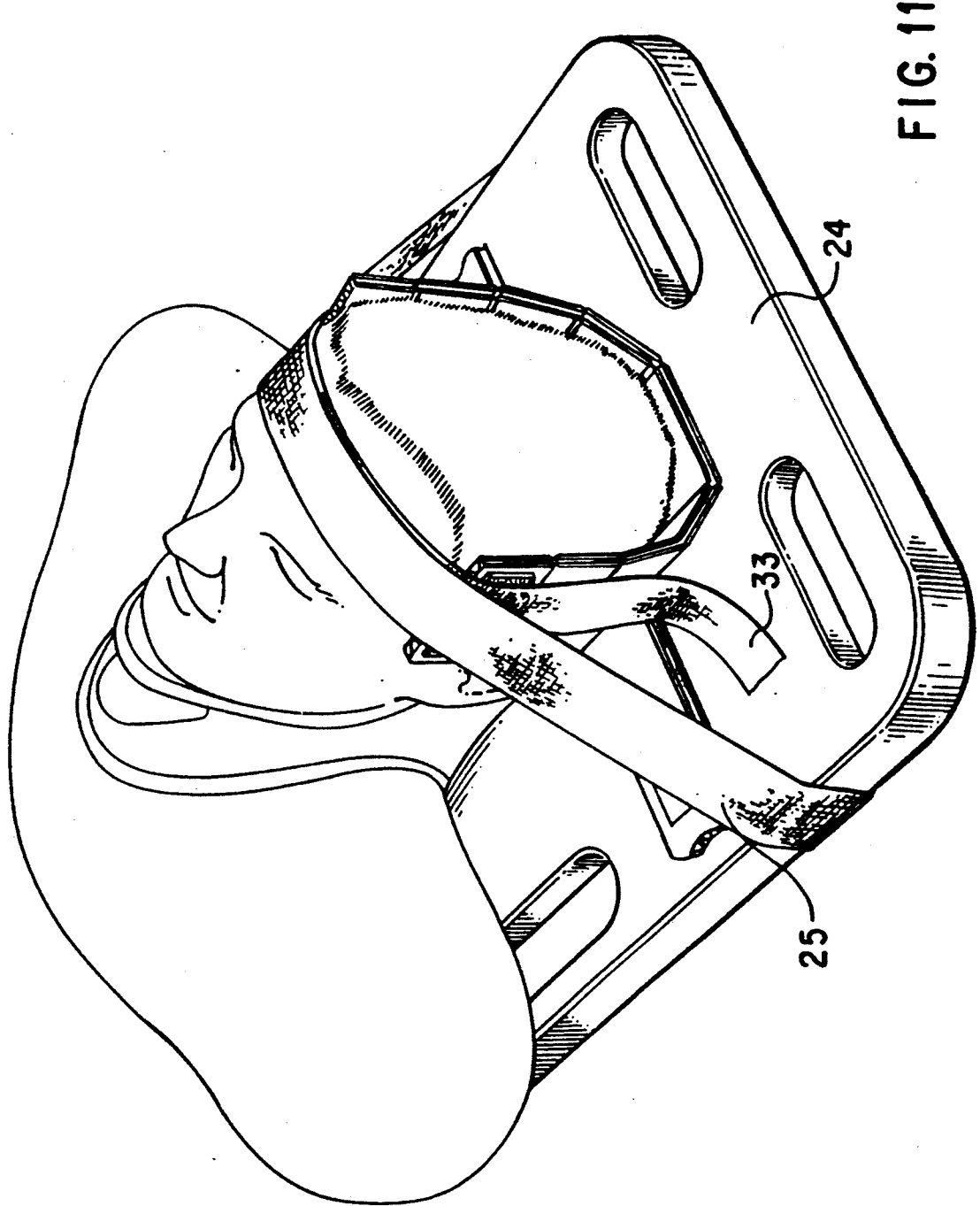

FIGS. 9 through 11 depict yet another embodiment of the device of the present invention which employs yet another configuration to restrain the patient's head. In this embodiment, a hook-and-loop patch 32 is placed on the underside of each side panel 17 toward the free ends. Only one of such patches is visible in FIG. 9. The side panels are held in the proper restraining conformation about the patient's head by joining the patches 21 with a hook-and-loop strap 33 which crosses from one patch, across the patient's forehead, to the opposite patch as shown in FIG. 10. A strip of tape 25 is then used as previously described to further immobilize the patient's head as shown in FIG. 11. With this restraining configuration, the same immobilization previously described in achieved.

This device is economical to manufacture because it is constructed from a single sheet of material. Furthermore, the size, shape and conformation of the side panels with respect to the foundation panel can provide easy access to the ears and the sides of the patient's head.

Devices of the present invention can be constructed from any sheet material with enough structural integrity to resist tearing while acting as a taping platform. Preferably, the devices are constructed from corrugated cardboard or another suitable material.

From the foregoing, it will be obvious to those skilled in the art that various modifications in the above-described devices and methods can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A head immobilization device comprising:
   a foundation portion including a slot and having a foundation panel;
   a restraining portion joined to said foundation portion, said restraining portion having a base panel, two side panels each extending laterally from said base panel and having a free end opposite the end of said panels which connects to said base panel, and a first engaging means associated with said free end of at least one of said side panels for engagement of at least said free end of the opposite side panel and for securing said side panels into secure and proper conformation so as to at least partially immobilize the head of a patient placed between said side panels; and
   wherein said foundation portion further comprises a strip of adhesive tape for acting as a second engaging means situated on the underside of said foundation panel for affixing said foundation panel to a spine board, and the adhesive tape is covered with a backing material that terminates in a tab that is threaded through said slot.

2. The device of claim 1 wherein said means for attaching said foundation portion to a spine board further comprises:
   a backing material covering the adhesive surface of said at least one adhesive strip and having a tab portion which extends free of said adhesive surface; and
   a slot in and through said foundation portion through which said tab portion of said backing material can extend such that it can be grasped.

3. A head immobilization device comprising:
   a foundation portion having a foundation panel;
   a restraining portion joined to said foundation portion, said restraining portion having a base panel, two side panels each extending laterally from said base panel and having a free end opposite the end of said panels which connects to said base panel, and a first engaging means associated with said free end of at least one of said side panels for engagement of at least said free end of the opposite side panel and for securing said side panels into secure and proper conformation so as to at least partially immobilize the head of a patient placed between said side panels, wherein said first engaging means comprises:
   at least one adhesive strip having a backing material covering its adhesive surface, said backing material having a tab portion which extends free of said adhesive surface; and
   a slot in and through said restraining portion through which said tab portion of said backing material can extend such that it can be grasped.

4. The device of claim 1 wherein said first engaging means comprises a strap made of hook and loop material.

5. The device of claim 4 wherein said opposite side panel is fitted with a patch of hook and loop material which can be engaged with said strap.

6. The device of claim 1 wherein said first engaging means is a strip of adhesive tape.

7. The device of claim 1 further comprising a band of material sized so that it can be extended from one lateral side of a spine board across the head of the patient to the other lateral side of a spine board.

8. The device of claim 7 wherein said band of material comprises an additional piece of adhesive tape.

* * * * *